(12) United States Patent
Nappa et al.

(10) Patent No.: US 9,139,498 B2
(45) Date of Patent: Sep. 22, 2015

(54) CATALYTICAL SYNTHESIS OF HYDROHALOCARBONS

(75) Inventors: Mario Joseph Nappa, Newark, DE (US); Ekaterina N Swearingen, Wilmington, DE (US); Sergei Rafailovich Sterlin, Moscow (RU)

(73) Assignee: THE CHEMOURS COMPANY FC, LLC, Wilmington, DE (US)

( * ) Notice: Subject to any disclaimer, the term of this patent is extended or adjusted under 35 U.S.C. 154(b) by 108 days.

(21) Appl. No.: 13/988,121

(22) PCT Filed: Nov. 7, 2011

(86) PCT No.: PCT/US2011/059500
§ 371 (c)(1),
(2), (4) Date: Jun. 13, 2013

(87) PCT Pub. No.: WO2012/067865
PCT Pub. Date: May 24, 2012

(65) Prior Publication Data
US 2014/0058141 A1  Feb. 27, 2014

(30) Foreign Application Priority Data
Nov. 17, 2010 (RU) .................... 2010147002

(51) Int. Cl.
 *C07C 17/278* (2006.01)
 *C07C 19/10* (2006.01)
 *C07C 17/383* (2006.01)

(52) U.S. Cl.
 CPC ............. *C07C 17/278* (2013.01); *C07C 17/383* (2013.01); *C07C 19/10* (2013.01)

(58) Field of Classification Search
 CPC .............................. C07C 17/278; C07C 19/10
 USPC ................................................... 570/172, 257
 See application file for complete search history.

(56) References Cited

U.S. PATENT DOCUMENTS

| 4,691,065 | A  | * | 9/1987 | Dannels ........................ 570/139 |
| 6,291,730 | B1 | * | 9/2001 | Baker et al. ................... 570/176 |
| 2006/1224441 | | | 6/2006 | Tung |
| 2008/0091053 | A1 | * | 4/2008 | Tung et al. .................... 570/153 |

FOREIGN PATENT DOCUMENTS

| EP | 1908744 A1 | 4/2008 |
| WO | 9705089 A1 | 2/1997 |

OTHER PUBLICATIONS

International Search Report and Written Opinion, PCT/US2011/059500, Mailing Date Jan. 31, 2012.
Vanderpuy, Trifluoroethylation of olefins with trichlorotrifluoroethane, Journal of Fluorine Chemistry, vol. 61, 1993 133-14.
Kotora et al., Selective additions of polyhalogenated compounds to chloro substituted ethenes catalyzed by a copper complex, Reaction Kinetics and Catalysis Letters, vol. 44, No. 2, 1991, 415-419.

* cited by examiner

*Primary Examiner* — Jafar Parsa
*Assistant Examiner* — Mendhanit Bahta

(57) ABSTRACT

A process is disclosed for producing addition compound $CF_3CCl_2CH_2CClXR$, wherein X=H, F, Cl or Br, and R=H or a perhalogenated alkyl group, provided that X and R are not both H. The process involves a liquid phase reaction of 1,1,1-trichlorotrifluoroethane with $CH_2$=CXR in the presence of an addition catalyst.

9 Claims, No Drawings

CATALYTICAL SYNTHESIS OF HYDROHALOCARBONS

BACKGROUND

1. Field of the Disclosure

This disclosure relates in general to the catalytical addition reactions of 1,1,1-trichlorotrifluoroethane ($CF_3CCl_3$, CFC-113a) with a hydrohaloolefin.

2. Description of Related Art

Halogenated alkanes, such as CFCs (chlorofluorocarbons) and HCFCs (hydrochlorofluorocarbons), have been employed in a wide range of applications, including their use as aerosol propellants, refrigerants, cleaning agents, expansion agents for thermoplastic and thermoset foams, heat transfer media, gaseous dielectrics, fire extinguishing and suppression agents, power cycle working fluids, polymerization media, particulate removal fluids, carrier fluids, buffing abrasive agents, and displacement drying agents. They are also useful as intermediates to more highly fluorinated compounds such as HFCs (hydrofluorocarbons) and HFOs (hydrofluoroolefins). Due to the concerns of ozone depletion caused by some of the CFC and HCFC products, HFCs have replaced CFCs and HCFCs in a number of applications including using as refrigerants or foam expansion agents. HFOs have been regarded as good candidates to replace traditional CFCs, HCFCs and HFCs since they are both ozone-friendly and having low global warming potentials (GWPs).

BRIEF SUMMARY OF THE DISCLOSURE

The present disclosure provides a liquid phase process to produce a product mixture comprising addition compound $CF_3CCl_2CH_2CClXR$, wherein X=H, F, Cl or Br, and R=H or a perhalogenated alkyl group, provided that X and R are not both H. The process comprises reacting 1,1,1-trichlorotrifluoroethane with $CH_2$=CXR in the presence of an addition catalyst.

DETAILED DESCRIPTION

The foregoing general description and the following detailed description are exemplary and explanatory only and are not restrictive of the invention, as defined in the appended claims. Other features and benefits of any one or more of the embodiments will be apparent from the following detailed description, and from the claims.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, use of "a" or "an" are employed to describe elements and components described herein. This is done merely for convenience and to give a general sense of the scope of the invention. This description should be read to include one or at least one and the singular also includes the plural unless it is obvious that it is meant otherwise.

Unless otherwise defined, all technical and scientific terms used herein have the same meaning as commonly understood by one of ordinary skill in the art to which this invention belongs. Although methods and materials similar or equivalent to those described herein can be used in the practice or testing of embodiments of the present invention, suitable methods and materials are described below. All publications, patent applications, patents, and other references mentioned herein are incorporated by reference in their entirety, unless a particular passage is cited. In case of conflict, the present specification, including definitions, will control. In addition, the materials, methods, and examples are illustrative only and not intended to be limiting.

Disclosed is a liquid phase process comprising reacting 1,1,1-trichlorotrifluoroethane with $CH_2$=CXR in the presence of an addition catalyst to produce a product mixture comprising addition compound $CF_3CCl_2CClXR$, wherein X=H, F, Cl or Br, and R=H or a perhalogenated alkyl group, provided that X and R are not both H.

The starting materials for the addition reactions in this disclosure, i.e., 1,1,1-trichlorotrifluoroethane and $CH_2$=CXR, can be synthesized by methods known in the art.

The term "alkyl", as used herein, either alone or in compound words such as "perhalogenated alkyl group", includes cyclic or acyclic and straight-chain or branched alkyl groups, such as, methyl, ethyl, n-propyl, i-propyl, or the different isomers thereof.

The term "perhalogenated alkyl group", as used herein, means an alkyl group wherein all hydrogens on carbon atoms have been substituted by halogens such as F, Cl, Br and I. Examples of a perhalogenated alkyl group include —$CF_3$ and —$CF_2CF_3$.

The term "addition catalyst", as used herein, means a catalyst that can promote addition reactions.

In some embodiments of this invention, X=H, F or Cl. In some embodiments of this invention, $CH_2$=CXR is selected from the group consisting of $CF_3CH$=$CH_2$, $CF_3CF_2CH$=$CH_2$, $CF_3CF$=$CH_2$ and $ClCH$=$CH_2$.

Examples of addition compound $CF_3CCl_2CH_2CClXR$ in this disclosure include $CF_3CCl_2CH_2CHClCF_3$, $CF_3CCl_2CH_2CHClCF_2CF_3$, $CF_3CCl_2CH_2CFClCF_3$ and $CF_3CCl_2CH_2CHCl_2$.

In some embodiments of this invention, $CH_2$=CXR is $CF_3CH$=$CH_2$ and the resulting product $CF_3CCl_2CH_2CClXR$ is $CF_3CCl_2CH_2CHClCF_3$.

In some embodiments of this invention, $CH_2$=CXR is $CF_3CF_2CH$=$CH_2$ and the resulting product $CF_3CCl_2CH_2CClXR$ is $CF_3CCl_2CH_2CHClCF_2CF_3$.

In some embodiments of this invention, $CH_2$=CXR is $CF_3CF$=$CH_2$ and the resulting product $CF_3CCl_2CH_2CClXR$ is $CF_3CCl_2CH_2CFClCF_3$.

In some embodiments of this invention, $CH_2$=CXR is $ClCH$=$CH_2$ and the resulting product $CF_3CCl_2CH_2CClXR$ is $CF_3CCl_2CH_2CHCl_2$.

The addition reaction involving 1,1,1-trichlorotrifluoroethane and $CH_2$=CXR in this disclosure is based on a stoichiometry of 1 mole of 1,1,1-trichlorotrifluoroethane per mole of $CH_2$=CXR. In practice, an excess of 1,1,1-trichlorotrifluoroethane may be used as desired. Typically, the mole ratio of 1,1,1-trichlorotrifluoroethane to $CH_2$=CXR is about 1:1 to about 10:1.

The addition reaction process of this disclosure may be practiced by putting 1,1,1-trichlorotrifluoroethane and $CH_2$=CXR starting materials and the addition catalysts into a reaction vessel and then heating the mixture with agitation. The process may be carried out by either the batchwise or continuous system.

At the end of the addition reaction, the desired product $CF_3CCl_2CH_2CClXR$ may be recovered from the product mixture by conventional methods. In some embodiments of this invention, the solid residues may be removed at the end of the addition reaction by decantation or filtration and the desired product may be purified or recovered by distillation of the resulting liquid product mixture.

In some embodiments of this invention, the addition catalyst is a copper catalyst comprising cupric chloride and a suitable reductant.

As used herein, cupric chloride can be either anhydrous ($CuCl_2$) or hydrated (e.g., $CuCl_2.2H_2O$). In some embodiments of this invention, the amount of $CuCl_2.2H_2O$ used in the addition reactions is from about 0.5 to about 10 weight percent based on the total weight of the starting materials (i.e., 1,1,1-trichlorotrifluoroethane and $CH_2$=CXR). In some embodiments of this invention, the amount of $CuCl_2.2H_2O$ used in the addition reactions is from about 1 to about 5 weight percent based on the total weight of the starting materials. In some embodiments of this invention, the amount of $CuCl_2$ used in the addition reactions is from about 0.4 to about 8 weight percent based on the total weight of the starting materials. In some embodiments of this invention, the amount of $CuCl_2$ used in the addition reactions is from about 0.8 to about 4 weight percent based on the total weight of the starting materials.

A suitable reductant in this disclosure is a reductant which can reduce Cu(II) compounds (e.g, $CuCl_2$) to Cu(I) compounds (e.g, CuCl), but will not react with the starting materials 1,1,1-trichlorotrifluoroethane and $CH_2$=CXR under the reaction conditions in this disclosure. In some embodiments of this invention, about stoichiometric amount of the reductant is used in the addition reactions of this disclosure. In some embodiments of this invention, more than stoichiometric amount of the reductant is used in the addition reactions of this disclosure.

Examples of suitable reductants include hydrazine ($N_2H_4$) and its derivatives such as monomethylhydrazine ($CH_3$(NH)$NH_2$) and 1,1-dimethylhydrazine (($CH_3$)$_2NNH_2$) et al., dithionites such as $Na_2S_2O_4$, $K_2S_2O_4$ and $(NH_4)_2S_2O_4$ et al., copper (zero valence, e.g, copper powder) and manganese (zero valence), and iron (zero valence, e.g, iron powder). In some embodiments of this invention, a low molecular weight nitrile such as acetonitrile and propionitrile can also be used as a suitable reductant.

Typically, a solvent is used together with the copper catalyst in this disclosure. In some embodiments of this invention, the solvent is a low molecular weight nitrile such as acetonitrile and propionitrile. In some embodiments of this invention, the solvent is an amide selected from the group consisting of dimethylformamide (DMF), dimethylacetamide and N-methylpyrrolidone.

Optionally, a co-catalyst can be used together with the copper catalyst in the addition reactions of this disclosure. Suitable co-catalysts are those which can form coordination compounds with Cu(I) or Cu(II). Examples of suitable co-catalysts for copper catalyst systems include bis(oxazoline)s, 2,2-bipyridine and their derivatives.

When the addition reaction in this disclosure is conducted in the presence of a copper catalyst, the temperature employed typically ranges from about 60° C. to about 240° C. In some embodiments of this invention, the temperature employed in such addition reaction ranges from about 130° C. to about 190° C. The pressure employed in the addition reaction is not critical. Typically, the addition reaction is conducted under autogenous pressure.

In some embodiments of this invention, the addition catalyst is an iron catalyst comprising iron and ferric chloride.

As used herein, ferric chloride can be either anhydrous ($FeCl_3$) or hydrated (e.g., $FeCl_3.6H_2O$). Iron used herein is metal iron having zero valence. In some embodiments of this invention, iron powder is used for the addition reaction. Typically, the molar ratio of iron to ferric chloride used in the addition reactions of this disclosure is from about 1:1 to about 10:1. In some embodiments of this invention, the total amount of iron and $FeCl_3$ used in the addition reaction is from about 5 to about 30 weight percent based on the amount of 1,1,1-trichlorotrifluoroethane.

Typically, a co-catalyst is used together with the iron catalyst in the addition reactions of this disclosure. In some embodiments of this invention, the co-catalyst is an alkyl or aryl phosphate such as triethyl phosphate, tributyl phosphate, phenyl diethyl phosphate, diethyl phosphate, dibutyl phosphate, phenyl phosphate, butyl phosphate and the like. Typically, the molar ratio of iron catalyst to phosphate co-catalyst is from about 2:1 to about 20:1. In some embodiments of this invention, the molar ratio of iron catalyst to phosphate co-catalyst is from about 5:1 to about 10:1.

Optionally, a solvent can be used together with the iron catalyst in this disclosure. In some embodiments of this invention, the starting material 1,1,1-trichlorotrifluoroethane can also be used as a solvent. In some embodiments of this invention, the solvent is an inert chemical compound which does not react with other chemical compounds or catalysts during the reaction. Such inert solvent, if used, should boil at a temperature enabling separation from the unconverted starting materials 1,1,1-trichlorotrifluoroethane and $CH_2$=CXR and from the product $CF_3CCl_2CH_2CClXR$.

When the addition reaction in this disclosure is conducted in the presence of an iron catalyst, the temperature employed typically ranges from about 60° C. to about 240° C. In some embodiments of this invention, the temperature employed in such addition reaction ranges from about 130° C. to about 190° C. The pressure employed in the addition reaction is not critical. Typically, the addition reaction is conducted under autogenous pressure.

The reactors, distillation columns, and their associated feed lines, effluent lines, and associated units used in applying the processes of embodiments of this invention may be constructed of materials resistant to corrosion. Typical materials of construction include Teflon™ and glass. Typical materials of construction also include stainless steels, in particular of the austenitic type, the well-known high nickel alloys, such as Monel™ nickel-copper alloys, Hastelloy™ nickel-based alloys and, Inconel™ nickel-chromium alloys, and copper-clad steel.

Many aspects and embodiments have been described above and are merely exemplary and not limiting. After reading this specification, skilled artisans appreciate that other aspects and embodiments are possible without departing from the scope of the invention.

EXAMPLES

The concepts described herein will be further described in the following examples, which do not limit the scope of the invention described in the claims.

Example 1

Example 1 demonstrates that addition reaction of $CF_3CCl_3$ with $CF_3CH$=$CH_2$ in the presence of a copper catalyst generates addition compound $CF_3CCl_2CH_2CHClCF_3$.

21.25 g of $CuCl_2 \cdot 2H_2O$, 13.5 g of phenylhydrazine, 75 ml of acetonitrile and 522 g (2.8 moles) of $CF_3CCl_3$ were loaded into a 1 L Hastelloy™ autoclave. The autoclave was cooled, evacuated and charged with 120 g of $CF_3CH\!=\!CH_2$. The reaction mixture was warmed up to 185° C. and kept at this temperature for 20 hrs. The distillation of the product mixture gave 150 g of desired product $CF_3CCl_2CH_2CHClCF_3$ (bp 54° C./100 mm Hg). The yield of $CF_3CCl_2CH_2CHClCF_3$ was 42%.

Example 2

Example 2 demonstrates that addition reaction of $CF_3CCl_3$ with $CF_3CH\!=\!CH_2$ in the presence of an iron catalyst generates addition compound $CF_3CCl_2CH_2CHClCF_3$.

7 g of iron powder, 7 g of tributyl phosphate, 4 g of $FeCl_3$ and 140 g (0.75 mole) of $CF_3CCl_3$ were loaded into a 400 ml Hastelloy™ tube. The tube was cooled, evacuated and charged with 48 g (0.5 mole) of $CF_3CH\!=\!CH_2$. The reaction mixture was warmed up to 150° C. and kept at this temperature for 3 hrs. The product mixture was distilled to give desired product $CF_3CCl_2CH_2CHClCF_3$ (bp 54° C./100 mm Hg) with 75% yield.

Example 3

Example 3 demonstrates that addition reaction of $CF_3CCl_3$ with $CF_3CF_2CH\!=\!CH_2$ in the presence of an iron catalyst generates addition compound $CF_3CCl_2CH_2CHClCF_2CF_3$.

6 g of iron powder, 6 g of tributyl phosphate, 3.5 g of $FeCl_3$ and 135 g (0.72 mole) of $CF_3CCl_3$ were loaded into a 400 ml Hastelloy™ tube. The tube was cooled, evacuated and charged with 45 g (0.3 mole) of $CF_3CF_2CH\!=\!CH_2$. The reaction mixture was warmed up to 150° C. and kept at this temperature for 3 hrs. The distillation of the product mixture gave desired product $CF_3CCl_2CH_2CHClCF_2CF_3$ (bp 70° C./90 mm Hg) with 63% yield.

Example 4

Example 4 demonstrates that addition reaction of $CF_3CCl_3$ with $CF_3CF\!=\!CH_2$ in the presence of an iron catalyst generates addition compound $CF_3CCl_2CH_2CFClCF_3$.

7 g of iron powder, 7 g of tributyl phosphate, 4 g of $FeCl_3$ and 112 g (0.6 mole) of $CF_3CCl_3$ were loaded into a 400 ml Hastelloy™ tube. The tube was cooled, evacuated and charged with 40.8 g (0.35 mole) of $CF_3CF\!=\!CH_2$. The reaction mixture was warmed up to 150° C. and kept at this temperature for 3 hrs. The product mixture was distilled to give desired product $CF_3CCl_2CH_2CFClCF_3$ (bp 57.9° C./80 mm Hg) with 60% yield.

Example 5

Example 5 demonstrates that addition reaction of $CF_3CCl_3$ with vinyl chloride ($ClCH\!=\!CH_2$) in the presence of a copper catalyst generates addition compound $CF_3CCl_2CH_2CHCl_2$.

A mixture of $CF_3CCl_3$ (150 g, 0.80 mol), vinyl chloride (9.15 g, 0.147 mol), $CuCl_2 \cdot 2H_2O$ (3.3 g, 19 mmol), copper powder (1.1 g, 17.3 mmol) and $CH_3CN$ (10 ml) was shaken in a 200 ml stainless steel autoclave at 170° C. to 175° C. for 17 hours. The conversion of vinyl chloride was complete. The product mixture was decanted from the solid residue, evaporated and then distilled under reduced pressure to give 32.6 g of a fraction which boiled at (38-157° C.) under 30 mm Hg pressure. GLC analysis indicated that the fraction contained 88.35 mole % of $CF_3CCl_2CH_2CHCl_2$ which represented 78% yield of $CF_3CCl_2CH_2CHCl_2$ based on the amount of vinyl chloride. The fraction above was further distilled to recover $CF_3CCl_2CH_2CHCl_2$ having boiling point of 146-147° C. under atmospheric pressure.

Note that not all of the activities described above in the general description or the examples are required, that a portion of a specific activity may not be required, and that one or more further activities may be performed in addition to those described. Still further, the order in which activities are listed are not necessarily the order in which they are performed.

In the foregoing specification, the concepts have been described with reference to specific embodiments. However, one of ordinary skill in the art appreciates that various modifications and changes can be made without departing from the scope of the invention as set forth in the claims below. Accordingly, the specification is to be regarded in an illustrative rather than a restrictive sense, and all such modifications are intended to be included within the scope of invention.

Benefits, other advantages, and solutions to problems have been described above with regard to specific embodiments. However, the benefits, advantages, solutions to problems, and any feature(s) that may cause any benefit, advantage, or solution to occur or become more pronounced are not to be construed as a critical, required, or essential feature of any or all the claims.

It is to be appreciated that certain features are, for clarity, described herein in the context of separate embodiments, may also be provided in combination in a single embodiment. Conversely, various features that are, for brevity, described in the context of a single embodiment, may also be provided separately or in any subcombination. Further, reference to values stated in ranges include each and every value within that range.

What is claimed is:

1. A liquid phase process comprising reacting 1,1,1-trichlorotrifluoroethane with $CH_2\!=\!CXR$ in the presence of an addition catalyst to produce a product mixture comprising addition compound $CF_3CCl_2CH_2CClXR$, wherein X=H, F, Cl or Br, and R=H or a perhalogenated alkyl group, provided that X and R are not both H, wherein the catalyst is not a copper catalyst and $CH_2\!=\!CXR$ is selected from the group consisting of $CF_3CH\!=\!CH_2$, $CF_3CF_2CH\!=\!CH_2$, and $CF_3CF\!=\!CH_2$
and provided that
when said CH2=CXR is CF3CH=CH2, said addition compound CF3CCl2CH2CClXR is CF3CCl2CH2CHClCF3;
when said CH2=CXR is CF3CF2CH=CH2, said addition compound CF3CCl2CH2CClXR is CF3CCl2CH2CHClCF2CF3; and
when said CH2=CXR is CF3CF=CH2 and said addition compound CF3CCl2CH2CClXR is CF3CCl2CH2CFClCF3.

2. The liquid phase process of claim 1 wherein said reaction is conducted at the temperature of from about 60° C. to about 240° C.

3. The liquid phase process of claim 1 wherein said addition catalyst is an iron catalyst comprising iron and ferric chloride.

4. The liquid phase process of claim 3 wherein said ferric chloride is anhydrous $FeCl_3$.

5. The liquid phase process of claim 3 wherein a co-catalyst is used together with said iron catalyst and wherein said co-catalyst is an alkyl or aryl phosphate.

6. The liquid phase process of claim 5 wherein said co-catalyst is selected from the group consisting of triethyl phosphate, tributyl phosphate, phenyl diethyl phosphate, diethyl phosphate, dibutyl phosphate, phenyl phosphate and butyl phosphate.

7. The liquid phase process of claim 3 wherein said reaction is conducted at the temperature of from about 60° C. to about 240° C.

8. The liquid phase process of claim 1 further comprising recovering said addition compound $CF_3CCl_2CH_2CClXR$ from the product mixture.

9. The liquid phase process of claim 8 wherein said addition compound $CF_3CCl_2CH_2CClXR$ is recovered from the product mixture by distillation.

* * * * *